(12) United States Patent
Bender et al.

(10) Patent No.: US 7,227,034 B2
(45) Date of Patent: Jun. 5, 2007

(54) PROCESS FOR ARYLAMINE PRODUCTION

(75) Inventors: Timothy P. Bender, Port Credit (CA); Jennifer A. Coggan, Cambridge (CA)

(73) Assignee: Xerox Corporation, Stamford, CT (US)

( * ) Notice: Subject to any disclaimer, the term of this patent is extended or adjusted under 35 U.S.C. 154(b) by 439 days.

(21) Appl. No.: 10/992,687

(22) Filed: Nov. 22, 2004

(65) Prior Publication Data

US 2006/0111583 A1    May 25, 2006

(51) Int. Cl.
- *C07C 227/16* (2006.01)
- *C07D 409/12* (2006.01)
- *C07D 213/127* (2006.01)

(52) U.S. Cl. ............... 562/497; 549/59; 546/264

(58) Field of Classification Search ........ 562/457; 549/59; 546/264
See application file for complete search history.

(56) References Cited

U.S. PATENT DOCUMENTS

| | | | |
|---|---|---|---|
| 4,265,990 A | 5/1981 | Stolka et al. | |
| 4,801,517 A | 1/1989 | Frechet et al. | |
| 5,723,671 A | 3/1998 | Goodbrand et al. | |
| 5,739,169 A * | 4/1998 | Ocain et al. | ........ 514/658 |
| 6,730,448 B2 | 5/2004 | Yoshino et al. | |
| 2003/0190546 A1 | 10/2003 | Yoshino et al. | |
| 2004/0086794 A1 | 5/2004 | Yamada et al. | |

FOREIGN PATENT DOCUMENTS

| | | |
|---|---|---|
| EP | 0 617 005 A2 | 9/1994 |
| EP | 0 755 916 A2 | 1/1997 |
| JP | A 57-128344 | 8/1982 |
| JP | B2 60-22347 | 6/1985 |
| JP | A-63-65449 | 3/1988 |
| JP | A-4-15659 | 1/1992 |
| JP | B2 5-47104 | 7/1993 |

* cited by examiner

*Primary Examiner*—Peter O'Sullivan
(74) *Attorney, Agent, or Firm*—Oliff & Berridge, PLC.

(57) ABSTRACT

Forming a 4-aminobiphenyl derivative arylamine compound, includes (i) providing a first disubstituted 4-aminobiphenyl compound; (ii) optionally formylating the first disubstituted 4-aminobiphenyl compound to form a bisformyl substituted compound where the first disubstituted 4-aminobiphenyl compound is not a bisformyl substituted compound; (iii) acidifying the bisformyl substituted compound to convert formyl functional groups into acid functional groups to form an acidified compound; and (iv) hydrogenating the acidified compound to saturate at least one unsaturated double bonds in the acidified compound.

23 Claims, 4 Drawing Sheets

PROCESS FOR ARYLAMINE PRODUCTION

BACKGROUND OF THE INVENTION

1. Field of Invention

This invention relates generally to improved chemical processes for the synthesis of arylamine compounds, and to the use of such arylamine compounds in producing overcoating layers for electrophotographic imaging members. In particular, this invention provides a process for forming a 4-aminobiphenyl derivative arylamine compound, such as N,N-[3-carboxypropyl phenyl]-4-aminobiphenyl or its alkali metal salt, using a direct hydrogenation reaction on a carboxylate salt.

2. Description of Related Art

In electrophotography, an electrophotographic substrate containing a photoconductive insulating layer on a conductive layer is imaged by first uniformly electrostatically charging a surface of the substrate. The substrate is then exposed to a pattern of activating electromagnetic radiation, such as, for example, light. The light or other electromagnetic radiation selectively dissipates the charge in illuminated areas of the photoconductive insulating layer while leaving behind an electrostatic latent image in non-illuminated areas of the photoconductive insulating layer. This electrostatic latent image is then developed to form a visible image by depositing finely divided electroscopic marking particles on the surface of the photoconductive insulating layer. The resulting visible image is then transferred from the electrophotographic substrate to a necessary member, such as, for example, an intermediate transfer member or a print substrate, such as paper. This image developing process can be repeated as many times as necessary with reusable photoconductive insulating layers.

In image forming apparatus such as copiers, printers and facsimiles, electrophotographic systems in which charging, exposure, development, transfer, etc. are carried out using electrophotographic photoreceptors have been widely employed. In such image forming apparatus, demands for speeding up of image formation processes, improvement in image quality, miniaturization and prolonged life of the apparatus, reduction in production cost and running cost, etc. are increasingly growing. Further, with recent advances in computers and communication technology, digital systems and color image output systems have been applied also to the image forming apparatus.

Electrophotographic imaging members (i.e. photoreceptors) are well known. Electrophotographic imaging members are commonly used in electrophotographic processes having either a flexible belt or a rigid drum configuration. These electrophotographic imaging members sometimes comprise a photoconductive layer including a single layer or composite layers. These electrophotographic imaging members take many different forms. For example, layered photoresponsive imaging members are known in the art. U.S. Pat. No. 4,265,990 to Stolka et al., which is incorporated herein by reference in its entirety, describes a layered photoreceptor having separate photogenerating and charge transport layers. The photogenerating layer disclosed in the 990 patent is capable of photogenerating holes and injecting the photogenerated holes into the charge transport layer. Thus, in the photoreceptors of the 990 patent, the photogenerating material generates electrons and holes when subjected to light.

More advanced photoconductive photoreceptors containing highly specialized component layers are also known. For example, a multilayered photoreceptor employed in electrophotographic imaging systems sometimes includes one or more of a substrate, and undercoating layer, an intermediate layer, an optional hole or charge blocking layer, a charge generating layer (including a photogenerating material in a binder) over an undercoating layer and/or a blocking layer, and a charge transport layer (including a charge transport material in a binder). Additional layers such as one or more overcoat layer or layers are also sometimes included.

In view of such a background, improvement in electrophotographic properties and durability, miniaturization, reduction in cost, etc., in electrophotographic photoreceptors have been studied, and electrophotographic photoreceptors using various materials have been proposed.

For example, JP-A-63-65449 (the term "JP-A" as used herein means an "unexamined published Japanese patent application"), which is incorporated herein by reference in its entirety, discloses an electrophotographic photoreceptor in which fine silicone particles are added to a photosensitive layer, and also discloses that such addition of the fine silicone particles imparts lubricity to a surface of the photoreceptor.

Further, in forming a photosensitive layer, a method has been proposed in which a charge transfer substance is dispersed in a binder polymer or a polymer precursor thereof, and then the binder polymer or the polymer precursor thereof is cured. JP-B-5-47104 (the term "JP-B" as used herein means an "examined Japanese patent publication") and JP-B-60-22347, which are incorporated herein by reference in their entirety, disclose electrophotographic photoreceptors using silicone materials as the binder polymers or the polymer precursors thereof.

Furthermore, in order to improve mechanical strength of the electrophotographic photoreceptor, a protective layer is formed on the surface of the photosensitive layer in some cases. A crosslinkable resin is used as a material for the protective layer in many cases. However, the protective layer formed by the crosslinkable resin acts as an insulating layer, which impairs the photoelectric characteristics of the photoreceptor. For this reason, a method of dispersing a fine conductive metal oxide powder (JP-A-57-128344) or a charge transfer substance (JP-A-4-15659) in the protective layer and a method of reacting a charge transfer substance having a reactive functional group with a thermoplastic resin to form the protective layer have been proposed. JP-A-57-128344 and JP-A-4-15659 are incorporated herein by reference in their entirety.

However, even the above-mentioned conventional electrophotographic photoreceptors are not necessarily sufficient in electrophotographic characteristics and durability, particularly when they are used in combination with a charger of the contact charging system (contact charger) or a cleaning apparatus such as a cleaning blade.

Further, when the photoreceptor is used in combination with the contact charger and a toner obtained by chemical polymerization (polymerization toner), a surface of the photoreceptor is stained with a discharge product produced in contact charging or the polymerization toner remaining after a transfer step to deteriorate image quality in some cases. Still further, the use of the cleaning blade in order to remove the discharge product adhered to the surface of the photoreceptor or the remaining toner increases friction and abrasion between the surface of the photoreceptor and the cleaning blade, resulting in a tendency to cause damage of the surface of the photoreceptor, breakage of the blade or turning up of the blade.

Furthermore, in producing the electrophotographic photoreceptor, in addition to improvement in electrophotographic characteristics and durability, it becomes an important problem to reduce production cost. However, in the case of the conventional electrophotographic photoreceptor, the problem is encountered that coating defects such as orange peel appearances and hard spots are liable to occur.

The use of silicon-containing compounds in photoreceptor layers, including in photosensitive and protective layers, has been shown to increase the mechanical lifetime of electrophotographic photoreceptors, under charging conditions and scorotron charging conditions. For example, U.S. Patent Application Publication US 2004/0086794 to Yamada et al., which is incorporated herein by reference in its entirety, discloses a photoreceptor having improved mechanical strength and stain resistance.

However, the above-mentioned conventional electrophotographic photoreceptor is not necessarily sufficient in electrophotographic characteristics and durability, particularly when it is used in an environment of high heat and humidity.

Photoreceptors having low wear rates, such as those described in US 2004/0086794, also have low refresh rates. The low wear and refresh rates are a primary cause of image deletion errors, particularly under conditions of high humidity and high temperature. U.S. Pat. No. 6,730,448 B2 to Yoshino et al., which is incorporated herein by reference in its entirety, addresses this issue in its disclosure of photoreceptors having some improvement in image quality, fixing ability, even in an environment of high heat and humidity. However, there still remains a need for electrophotographic photoreceptors having high mechanical strength and improved electrophotographic characteristics and improved image deletion characteristics even under conditions of high temperature and high humidity.

SUMMARY OF THE INVENTION

This invention provides a method for the preparation of an arylamine compound where the arylamine compound is a symmetric derivative of 4-aminobiphenyl. Specifically this invention provides a method whereby a derivative of 4-aminobiphenyl, preferably a symmetric arylamine derivative of 4-aminobiphenyl, can be made using direct hydrogenation of a precursor organic salt, rather than a longer multi-step synthesis procedure.

The arylamine derivative of 4-aminobiphenyl is further useful as an intermediate, which could be saponified to produce a dicarboxylic acid salt of an alkali earth compound. This dicarboxylic acid salt of an alkali earth compound can be further derivatized with an alkylhalide compound containing a siloxane moiety to produce a siloxane containing arylamine compound which is useful in the preparation of siloxane containing charge transporting layers for electrophotographic application.

These and other features and advantages of various exemplary embodiments of materials, devices, systems and/or methods according to this invention are described in, or are apparent from, the following detailed description of the various exemplary embodiments of the methods and systems according to this invention.

DETAILED DESCRIPTION OF PREFERRED EMBODIMENTS

Figure 1:
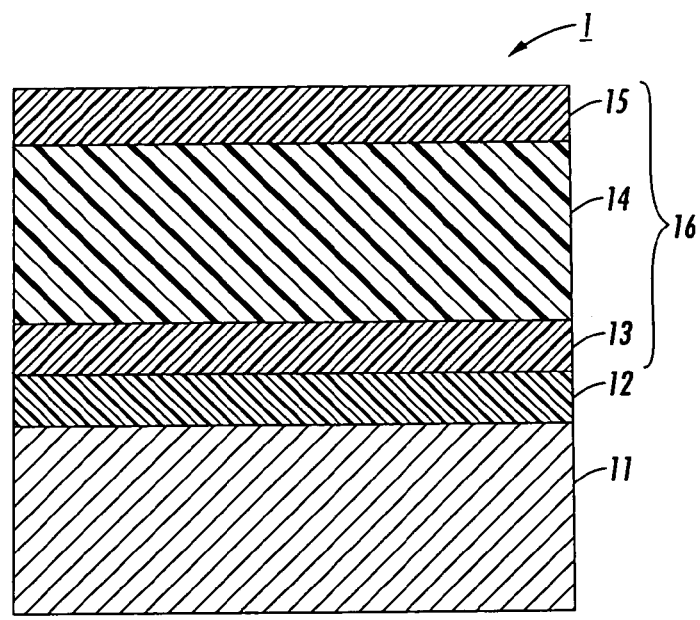
FIG. 1 is a schematic cross sectional view showing a preferred embodiment of an electrophotographic photoreceptor of the invention.

Preferred embodiments of the invention will be described in detail below with reference to drawings in some cases. In the drawings, the same reference numerals and signs are used to designate the same or corresponding parts, and repeated descriptions are avoided.

Electrophotographic Photoreceptor

In electrophotographic photoreceptors of embodiments, photosensitive layers comprise one or more silicon compound-containing layers, and the silicon compound-containing layers further contain resin.

In embodiments, the resin may be a resin soluble in a liquid component in a coating solution used for formation of this layer. Such a resin soluble in the liquid component may be selected based upon the kind of liquid component. For example, if the coating solution contains an alcoholic solvent (such as methanol, ethanol or butanol), a polyvinyl acetal resin such as a polyvinyl butyral resin, a polyvinyl formal resin or a partially acetalized polyvinyl acetal resin in which butyral is partially modified with formal or acetoacetal, a polyamide resin, a cellulose resin such as ethyl cellulose and a phenol resin may be suitably chosen as the alcohol-soluble resins. These resins may be used either alone or as a combination of two or more of them. Of the above-mentioned resins, the polyvinyl acetal resin is preferred in terms of electric characteristics.

In embodiments, the weight-average molecular weight of the resin soluble in the liquid component may be from about 2,000 to about 1,000,000, preferably from about 5,000 to about 50,000. When the average molecular weight is less than 2,000, the effect of enhancing discharge gas resistance, mechanical strength, scratch resistance, particle dispersibility, etc., tends to become insufficient. However, when the average molecular weight exceeds 1,000,000, the resin solubility in the coating solution decreases, and the amount of resin added to the coating solution may be limited and poor film formation in the production of the photosensitive layer may result.

Further, the amount of the resin soluble in the liquid component may be, in embodiments, from 0.1 to 15% by weight, or from 0.5 to 10% by weight, based on the total amount of the coating solution. When the amount added is less than 0.1% by weight, the effect of enhancing discharge gas resistance, mechanical strength, scratch resistance, particle dispersibility, etc. tends to become insufficient. However, if the amount of the resin soluble in the liquid component exceeds 15% by weight, there is a tendency for formation of indistinct images when the electrophotographic photoreceptor of the invention is used at high temperature and high humidity.

As used herein, a "high temperature environment" or "high temperature conditions" refer to an atmosphere in which the temperature is at least 28-30° C. A "high humidity environment" or "high humidity conditions" refer to an atmosphere in which the relative humidity is at least 75-80%.

There is no particular limitation on the silicon compound used in embodiments of the invention, as long as it has at least one silicon atom. However, a compound having two or more silicon atoms in its molecule may be used in embodiments. The use of the compound having two or more silicon atoms in its molecule allows both the strength and image quality of the electrophotographic photoreceptor to be achieved at higher levels.

In embodiments, at least one member selected from silicon-containing compounds represented by the following general formulas (2) to (4) and hydrolysates or hydrolytic condensates thereof is preferably used.

$$W^1(-SiR_{3-a}Q_a)_2 \quad (2)$$

$$W^2(-D-SiR_{3-a}Q_a)_b \quad (3)$$

$$SiR_{4-c}Q_c \quad (4)$$

In general formulas (2) to (4), $W^1$ represents a divalent organic group, $W^2$ represents an organic group derived from a compound having hole transport capability, R represents a member selected from the group consisting of a hydrogen atom, an alkyl group and a substituted or unsubstituted aryl group, Q represents a hydrolytic group, D represents a divalent group, a represents an integer of 1 to 3, b represents an integer of 2 to 4, and c represents an integer of 1 to 4.

R in general formulas (2) to (4) represents a hydrogen atom, an alkyl group (preferably an alkyl group having 1 to 5 carbon atoms) or a substituted or unsubstituted aryl group (preferably a substituted or unsubstituted aryl group having 6 to 15 carbon atoms), as described above.

Further, the hydrolytic group represented by Q in general formulas (2) to (4) means a functional group which can form a siloxane bond (O—Si—O) by hydrolysis in the curing reaction of the compound represented by any one of general formulas (2) to (4). Non-limiting examples of the hydrolytic groups that may be used in embodiments include a hydroxyl group, an alkoxyl group, a methyl ethyl ketoxime group, a diethylamino group, an acetoxy group, a propenoxy group and a chloro group. In particular embodiments, a group represented by —OR" (R" represents an alkyl group having 1 to 15 carbon atoms or a trimethylsilyl group) may be used.

In general formula (3), the divalent group represented by D may be, in embodiments, a divalent hydrocarbon group represented by $-C_nH_{2n}-$, $-C_nH_{2n-2}-$, $-C_nH_{2n-4}-$ (n is an integer of 1 to about 15, and preferably from 2 to about 10), $-CH_2-C_6H_4-$ or $-C_6H_4-C_6H_4-$, an oxycarbonyl group (—COO—), a thio group (—S—), an oxy group (—O—), an isocyano group (—N=CH—) or a divalent group in which two or more of them are combined. The divalent group may have a substituent group such as an alkyl group, a phenyl group, an alkoxyl group or an amino group on its side chain. When D is the above-mentioned preferred divalent group, proper flexibility may be imparted to an organic silicate skeleton, thereby tending to improve the strength of the layer.

Non-limiting examples of the compounds represented by the above-mentioned general formula (2) are shown in Table 1.

TABLE 1

| No. | Structural Formula |
|---|---|
| III-1 | $(MeO)_3Si-(CH_2)_2-Si(OMe)_3$ |
| III-2 | $(MeO)_2Me-(CH_2)_2-SiMe(OMe)_2$ |
| III-3 | $(MeO)_2MeSi-(CH_2)_6-SiMe(OMe)_2$ |
| III-4 | $MeO)_3Si-(CH_2)_6-Si(OMe)_3$ |
| III-5 | $(EtO)_3Si-(CH_2)_6-Si(OEt)_3$ |
| III-6 | $(MeO)_2MeSi-(CH_2)_{10}-SiMe(OMe)_2$ |
| III-7 | $(MeO)_3Si-(CH_2)_3-NH-(CH_2)_3-Si(OMe)_3$ |
| III-8 | $(MeO)_3Si-(CH_2)_3-NH-(CH_2)_2-NH-(CH_2)_3-Si(OMe)_3$ |
| III-9 |  |
| III-10 |  |
| III-11 |  |
| III-12 | (MeO)$_3$Si—CH$_2$-C$_6$H$_4$-CH$_2$-CH$_2$-C$_6$H$_4$-CH$_2$—Si(OMe)$_3$ |
| III-13 | (MeO)$_2$MeSi—CH$_2$-C$_6$H$_4$-CH$_2$-CH$_2$-C$_6$H$_4$-CH$_2$—SiMe(OMe)$_2$ |

TABLE 1-continued

| No. | Structural Formula |
|---|---|
| III-14 | 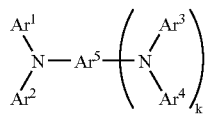 |
| III-15 | (MeO)₃SiC₃H₆—O—CH₂CH{—O—C₃H₆Si(OMe)₃}—CH₂{—O—C₃H₆Si(OMe)₃} |
| III-16 | (MeO)₃SiC₂H₄—SiMe₂—O—SiMe₂—O—SiMe₂—C₂H₄Si(OMe)₃ |

Further, in the above-mentioned general formula (3), there is no particular limitation on the organic group represented by $W^2$, as long as it is a group having hole transport capability. However, in particular embodiments, $W^2$ may be an organic group represented by the following general formula (6):

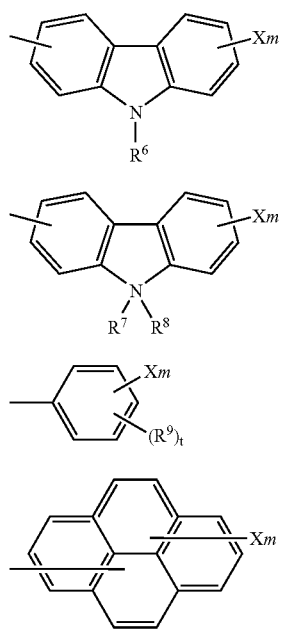

wherein $Ar^1$, $Ar^2$, $Ar^3$ and $Ar^4$, which may be the same or different, each represents a substituted or unsubstituted aryl group, $Ar^5$ represents a substituted or unsubstituted aryl or arylene group, k represents 0 or 1, and at least one of $Ar^1$ to $Ar^5$ has a bonding hand to connect with -D-SiR$_{3-a}$Q$_a$ in general formula (3).

$Ar^1$ to $Ar^4$ in the above-mentioned general formula (6) are each preferably any one of the following formulas (7) to (13):

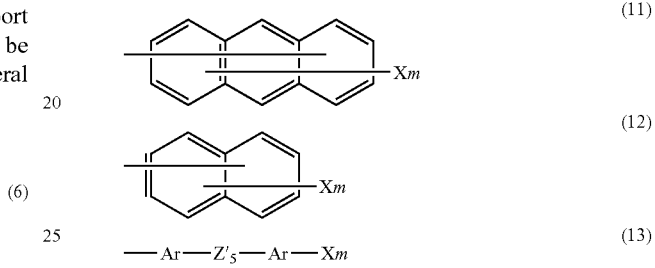

—Ar—Z'₅—Ar—Xm (13)

In formulas (7) to (13), $R^6$ represents a member selected from the group consisting of a hydrogen atom, an alkyl group having 1 to 4 carbon atoms, an unsubstituted phenyl group or a phenyl group substituted by an alkyl group having 1 to 4 carbon atoms or an alkoxyl group having 1 to 4 carbon atoms, and an aralkyl group having 7 to 10 carbon atoms; $R^7$ to $R^9$ each represents a member selected from the group consisting of a hydrogen atom, an alkyl group having 1 to 4 carbon atoms, an alkoxyl group having 1 to 4 carbon atoms, an unsubstituted phenyl group or a phenyl group substituted by an alkoxyl group having 1 to 4 carbon atoms, an aralkyl group having 7 to 10 carbon atoms, and a halogen atom; Ar represents a substituted or unsubstituted arylene group; X represents -D-SiR$_{3-a}$Q$_a$ in general formula (3); m and s each represents 0 or 1; q and r each represents an integer of 1 to 10; and t and t' each represents an integer of 1 to 3.

Here, Ar in formula (7) may be one represented by the following formula (14) or (15):

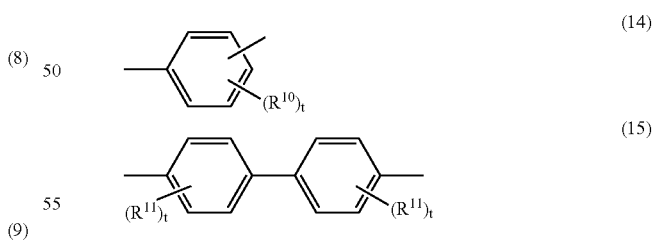

In formulas (14) and (15), $R^{10}$ and $R^{11}$ each represent a member selected from the group consisting of a hydrogen atom, an alkyl group having 1 to 4 carbon atoms, an alkoxyl group having 1 to 4 carbon atoms, an unsubstituted phenyl group or a phenyl group substituted by an alkoxyl group having 1 to 4 carbon atoms, an aralkyl group having 7 to 10 carbon atoms, and a halogen atom; and t represents an integer of 1 to 3.

Further, Z' in formula (13) is preferably one represented by any one of the following formulas (16) to (23):

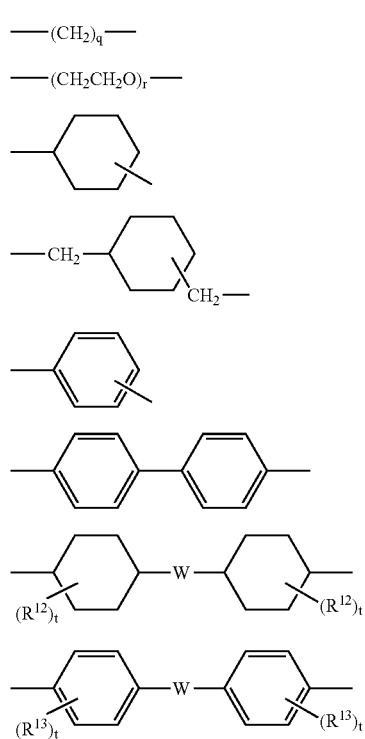

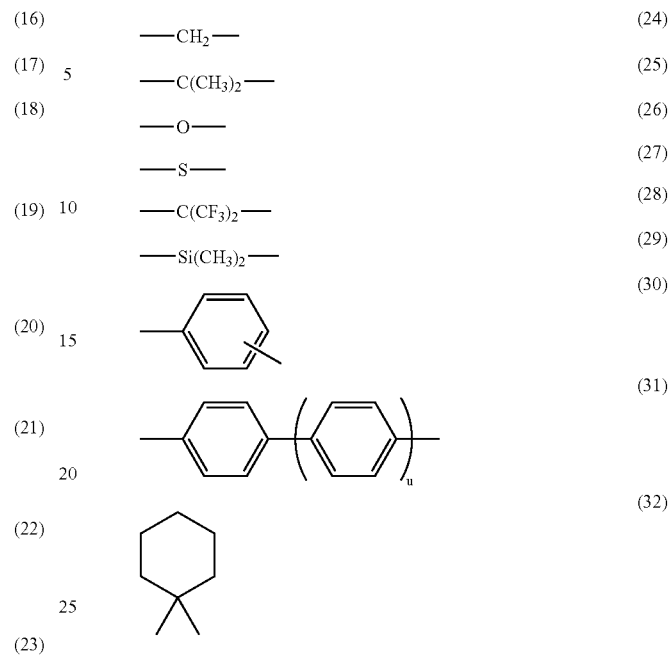

In formulas (16) to (23), $R^{12}$ and $R^{13}$ each represent a member selected from the group consisting of a hydrogen atom, an alkyl group having 1 to 4 carbon atoms, an alkoxyl group having 1 to 4 carbon atoms, an unsubstituted phenyl group or a phenyl group substituted by an alkoxyl group having 1 to 4 carbon atoms, an aralkyl group having 7 to 10 carbon atoms, and a halogen atom; W represents a divalent group; q and r each represents an integer of 1 to 10; and t represents an integer of 1 to 3.

W in the above-mentioned formulas (22) and (23) may be any one of divalent groups represented by the following formulas (24) to (32):

In formula (31), u represents an integer of 0 to 3.

Further, in general formula (6), $Ar^5$ is the aryl group illustrated in the description of $Ar^1$ to $Ar^4$, when k is 0, and an arylene group obtained by removing a certain hydrogen atom from such an aryl group, when k is 1.

Combinations of $Ar^1$, $Ar^2$, $Ar^3$, $Ar^4$, $Ar^5$ and integer k in formula (6) and a group represented by $-D-SiR_{3-a}Q_a$ in general formula (3) in particular exemplary embodiments are shown in Tables 2; additional exemplary embodiments can be found in US 2004/0086794 and U.S. Pat. No. 6,730,448 B2, the entire disclosures of which are incorporated herein by reference. In the tables, S represents $-D-Si R_{3-a}Q_a$ linked to $Ar^1$ to $Ar^5$, Me represents a methyl group, Et represents an ethyl group, and Pr represents a propyl group.

TABLE 2

| No. | $Ar^1$ | $Ar^2$ | $Ar^3$ & $Ar^4$ | $Ar^5$ | k | —S |
|---|---|---|---|---|---|---|
| V-1 | biphenyl | phenyl-S | — | phenyl-S | 0 | $-(CH_2)_2-COO-(CH_2)_3-Si(O^iPr)_3$ |
| V-2 | biphenyl | phenyl-S | — | phenyl-S | 0 | $-(CH_2)_2-COO-(CH_2)_3-SiMe(O^iPr)_2$ |
| V-3 | biphenyl | phenyl-S | — | phenyl-S | 0 | $-(CH_2)_2-COO-(CH_2)_3-SiMe_2(O^iPr)$ |
| V-4 | biphenyl | phenyl-S | — | phenyl-S | 0 | $-COO-(CH_2)_3-Si(O^iPr)_3$ |

TABLE 2-continued

| No. | Ar¹ | Ar² | Ar³ & Ar⁴ | Ar⁵ | k | —S |
|---|---|---|---|---|---|---|
| V-5 | 2,4-dimethylphenyl | biphenyl-S | — | biphenyl-S | O | —(CH$_2$)$_2$—COO—(CH$_2$)$_3$—Si(O$^i$Pr)$_3$ |
| V-6 | 2,4-dimethylphenyl | biphenyl-S | — | biphenyl-S | O | —(CH$_2$)$_2$—COO—(CH$_2$)$_3$—SiMe(O$^i$Pr)$_2$ |
| V-7 | 2,4-dimethylphenyl | biphenyl-S | — | biphenyl-S | O | —(CH$_2$)$_2$—COO—(CH$_2$)$_3$—SiMe$_2$(O$^i$Pr) |
| V-8 | 2,4-dimethylphenyl | biphenyl-S | — | biphenyl-S | O | —COO—(CH$_2$)$_3$—Si(O$^i$Pr)$_3$ |
| V-9 | phenyl-S | phenyl-S | — | phenyl-S | O | —(CH$_2$)$_2$—COO—(CH$_2$)$_3$—Si(O$^i$Pr)$_3$ |
| V-10 | phenyl-S | phenyl-S | — | phenyl-S | O | —(CH$_2$)$_2$—COO—(CH$_2$)$_3$—SiMe(O$^i$Pr)$_2$ |
| V-11 | phenyl-S | phenyl-S | — | phenyl-S | O | —(CH$_2$)$_2$—COO—(CH$_2$)$_3$—SiMe$_2$(O$^i$Pr) |
| V-12 | phenyl-S | phenyl-S | — | phenyl-S | O | —COO—(CH$_2$)$_3$—Si(O$^i$Pr)$_3$ |
| V-13 | biphenyl-S | biphenyl-S | — | biphenyl-S | O | —(CH$_2$)$_2$—COO—(CH$_2$)$_3$—Si(O$^i$Pr)$_3$ |
| V-14 | biphenyl-S | biphenyl-S | — | biphenyl-S | O | —(CH$_2$)$_2$—COO—(CH$_2$)$_3$—SiMe(O$^i$Pr)$_2$ |
| V-15 | biphenyl-S | biphenyl-S | — | biphenyl-S | O | —(CH$_2$)$_2$—COO—(CH$_2$)$_3$—SiMe$_2$(O$^i$Pr) |
| V-16 | biphenyl-S | biphenyl-S | — | biphenyl-S | O | —COO—(CH$_2$)$_3$—Si(O$^i$Pr)$_3$ |

Further, in embodiments, the silicon compounds represented by the above-mentioned general formula (4) may include silane coupling agents such as a tetrafunctional alkoxysilane (c=4) such as tetramethoxysilane or tetraethoxysilane; a trifunctional alkoxysilane (c=3) such as methyltrimethoxysilane, methyltriethoxysilane, ethyltrimethoxysilane, methyltrimethoxyethoxysilane, vinyltrimethoxysilane, vinyltriethoxysilane, phenyltrimethoxysilane, γ-glycidoxypropylmethyldiethoxysilane, γ-glycidoxypropyltrimethoxysilane, γ-glycidoxypropyltriethoxysilane, γ-aminopropyltriethoxysilane, γ-aminopropyltrimethoxysilane, γ-aminopropylmethyldimethoxysilane, N-β-(aminoethyl)-γ-aminopropyltriethoxysilane, (tridecafluoro-1,1,2,2-tetrahydrooctyl)triethoxysilane, (3,3,3-trifluoropropyl)trimethoxysilane, 3-(heptafluoroisopropoxy)propyltriethoxysilane, 1H,1H,2H,2H-perfluoroalkyltriethoxysilane, 1H,1H,2H,2H-perfluorodecyltriethoxysilane or 1H,1H,2H,2H-perfluorooctyltriethoxysilane; a bifunctional alkoxysilane (c=2) such as dimethyldimethoxysilane, diphenyldimethoxysilane or methylphenyldimethoxysilane; and a monofunctional alkoxysilane (c=1) such as trimethylmethoxysilane.

In order to improve the strength of the photosensitive layer, the trifunctional alkoxysilanes and the tetrafunctional alkoxysilanes may be used in embodiments, and in order to improve the flexibility and film forming properties, the monofunctional alkoxysilanes and the bifunctional alkoxysilanes may be used in embodiments.

Silicone hard coating agents containing these coupling agents can also be used in embodiments. Commercially available hard coating agents include KP-85, X-40-99740 and X-40-2239 (available from Shinetsu Silicone Co., Ltd.), and AY42-440, AY42-441 and AY49-208 (available from Toray Dow Corning Co., Ltd.).

In embodiments, the silicon compound-containing layer may contain either only one of the silicon compounds represented by the above-mentioned general formulas (2) and (4) or two or more of them. Further, the compounds represented by general formulas (2) to (4) may include a monofunctional compound (a compound in which a or c is 1), a bifunctional compound (a compound in which a or c is 2), a trifunctional compound (a compound in which a or c is 3) and a tetrafunctional compound (a compound in which a or c is 4). However, in particular embodiments, the number of silicon atoms derived from the silicon-containing compounds represented by the above-mentioned general formulas (2) to (4) in the silicon compound-containing layer satisfies the following equation (5):

$$(N_{a=3}+N_{c\geq3})/N_{total} \leq 0.5 \quad (5)$$

wherein $N_{a=3}$ represents the number of silicon atoms derived from $-SiR_{3-a}Q_a$ of the silicon compound represented by general formula (2) or (3) in which a is 3, $N_{c\geq3}$ represents the number of silicon atoms derived from the silicon compound represented by general formula (4) in which c is 3 or 4, and $N_{total}$ represents the total of the number of silicon atoms derived from $-SiR_{3-a}Q_a$ of the silicon compound represented by general formula (2) or (3) and the number of silicon atoms derived from the silicon compound represented by general formula (4). That is to say, the ratio of the silicon compounds contained is preferably set so that the number of silicon atoms derived from the trifunctional compound or the tetrafunctional compound becomes 0.5 or less based on the number of silicon atoms derived from the silicon-containing compounds represented by general formulas (2) to (4) (in the case of the compound represented by general formula (2) or (3), the silicon atoms are limited to ones derived from $-SiR_{3-a}Q_a$, and the same applies hereinafter). When the value of the left side of equation (5) exceeds 0.5, an indistinct image tends to be liable to occur at high temperature and high humidity. When the value of the left side of equation (5) is decreased, there is the possibility that it causes a decrease in strength. However, the use of the compound having two or more silicon atoms in its molecule can improve the strength.

In order to further improve the stain adhesion resistance and lubricity of embodiments of the electrophotographic photoreceptor, various fine particles can also be added to the silicon compound-containing layer. The fine particles may be used either alone or as a combination of two or more of them. Non-limiting examples of the fine particles include fine particles containing silicon, such as fine particles containing silicon as a constituent element, and specifically include colloidal silica and fine silicone particles.

Colloidal silica used in embodiments as the fine particles containing silicon in the invention is selected from an acidic or alkaline aqueous dispersion of the fine particles having an average particle size of 1 to 100 nm, or 10 to 30 nm, and a dispersion of the fine particles in an organic solvent such as an alcohol, a ketone or an ester, and generally, commercially available particles can be used.

There is no particular limitation on the solid content of colloidal silica in a top surface layer of the electrophotographic photoreceptor of embodiments of the invention. However, in embodiments, colloidal silica is used within the range of from about 1 to about 50% by weight, preferably from about 5 to about 30% by weight, based on the total solid content of the top surface layer, in terms of film forming properties, electric characteristics and strength.

The fine silicone particles used as the fine particles containing silicon in the invention are selected from silicone resin particles, silicone rubber particles and silica particles surface-treated with silicone, which are spherical and have an average particle size of from about 1 to 500 nm, preferably from about 10 to about 100 nm, and generally, commercially available particles can be used in embodiments.

In embodiments, the fine silicone particles are small-sized particles that are chemically inactive and excellent in dispersibility in a resin, and further are low in content as may be necessary for obtaining sufficient characteristics. Accordingly, the surface properties of the electrophotographic photoreceptor can be improved without inhibition of the crosslinking reaction. That is to say, fine silicone particles improve the lubricity and water repellency of surfaces of electrophotographic photoreceptors where incorporated into strong crosslinked structures, which may then be able to maintain good wear resistance and stain adhesion resistance for a long period of time. The content of the fine silicone particles in the silicon compound-containing layer of embodiments may be within the range of from about 0.1 to about 20% by weight, preferably from about 0.5 to about 10% by weight, based on the total solid content of the silicon compound-containing layer.

Other fine particles that may be used in embodiments of the invention include fine fluorine-based particles such as ethylene tetrafluoride, ethylene trifluoride, propylene hexafluoride, vinyl fluoride and vinylidene fluoride, and semiconductive metal oxides such as $ZnO-Al_2O_3$, $SnO_2-Sb_2O_3$, $In_2O_3-SnO_2$, $ZnO-TiO_2$, $MgO-Al_2O_3$, $FeO-TiO_2$, $TiO_2$, $SnO_2$, $In_2O_3$, $ZnO$ and $MgO$.

In conventional electrophotographic photoreceptors, when the above-mentioned fine particles are contained in the photosensitive layer, the compatibility of the fine particles with a charge transfer substance or a binding resin may become insufficient, which causes layer separation in the photosensitive layer, and thus forms an opaque film. As a result, the electric characteristics have deteriorated in some cases. In contrast, the silicon compound-containing layer of embodiments (a charge transfer layer in this case) may contain the resin soluble in the liquid component in the coating solution used for formation of this layer and the silicon compound, thereby improving the dispersibility of the fine particles in the silicon compound-containing layer. Accordingly, the pot life of the coating solution can be sufficiently prolonged, and it becomes possible to prevent deterioration of the electric characteristics.

Further, an additive such as a plasticizer, a surface modifier, an antioxidant, or an agent for preventing deterioration by light can also be used in the silicon compound-containing layer of embodiments. Non-limiting examples of plasticizers that may be used in embodiments include, for example, biphenyl, biphenyl chloride, terphenyl, dibutyl phthalate, diethylene glycol phthalate, dioctyl phthalate, triphenylphosphoric acid, methylnaphthalene, benzophenone, chlorinated paraffin, polypropylene, polystyrene and various fluorohydrocarbons.

The antioxidants may include an antioxidant having a hindered phenol, hindered amine, thioether or phosphite partial structure. This is effective for improvement of potential stability and image quality in environmental variation. The antioxidants include an antioxidant having a hindered phenol, hindered amine, thioether or phosphite partial structure. This is effective for improvement of potential stability and image quality in environmental variation. For example, the hindered phenol antioxidants include Sumilizer BHT-R, Sumilizer MDP-S, Sumilizer BBM-S, Sumilizer WX-R, Sumilizer NW, Sumilizer BP-76, Sumilizer BP-101, Sumilizer GA-80, Sumilizer GM and Sumilizer GS (the above are manufactured by Sumitomo Chemical Co., Ltd.), IRGANOX 1010, IRGANOX 1035, IRGANOX 1076, IRGANOX 1098, IRGANOX 1135, IRGANOX 1141, IRGANOX 1222, IRGANOX 1330, IRGANOX 1425WLj, IRGANOX 1520Lj, IRGANOX 245, IRGANOX 259, IRGANOX 3114, IRGANOX 3790, IRGANOX 5057 and IRGANOX 565 (the above are manufactured by Ciba Specialty Chemicals), and Adecastab AO-20, Adecastab AO-30, Adecastab AO-40, Adecastab AO-50, Adecastab AO-60, Adecastab AO-70, Adecastab AO-80 and Adecastab AO-330i (the above are manufactured by Asahi Denka Co., Ltd.). The hindered amine antioxidants include Sanol LS2626, Sanol LS765, Sanol LS770, Sanol LS744, Tinuvin 144, Tinuvin 622LD, Mark LA57, Mark LA67, Mark LA62, Mark LA68, Mark LA63 and Sumilizer TPS, and the phosphite antioxidants include Mark 2112, Mark PEP•8, Mark PEP•24G, Mark PEP•36, Mark 329K and Mark HP•10. Of these, the hindered phenol and hindered amine antioxidants are particularly preferred.

There is no particular limitation on the thickness of the silicon-containing layer, however, in embodiments, the silicon-containing layer may be in the range from about 2 to about 5 μm in thickness, preferably from about 2.7 to about 3.2 μm in thickness.

In embodiments of the invention, the photosensitive layer may comprise the silicon compound-containing layer as described above. In embodiments, the photosensitive has a peak area in the region of −40 to 0 ppm ($S_1$) and a peak area in the region of −100 to −50 ppm ($S_2$) in a $^{29}$Si- NMR spectrum that satisfy the following equation (1):

$$S_1/(S_1+S_2) \geq 0.5 \quad (1)$$

When $S_1/(S_1+S_2)$ is less than 0.5, defects are liable to occur. In particular, there is a tendency to cause an indistinct image at high temperature and the pot life shortened. Thus, $S_1/(S_1+S_2)$ may be about 0.6 or more, preferably about 0.7 or more.

The $^{29}$Si- NMR spectrum of the photosensitive layer can be measured through the following procedure. First, the photosensitive layer is separated from the electrophotographic photoreceptor by use of a silicon-free adhesive tape, and a sample tube (7 mm in diameter) made of zirconia is filled with 150 mg of the resulting separated product. The sample tube is set on a $^{29}$Si- NMR spectral measuring apparatus (for example, UNITY-300 manufactured by Varian, Inc.), and measurements are made under the following conditions:

Frequency: 59.59 MHz;
Delay time: 10.00 seconds;
Contact time: 2.5 milliseconds;
Measuring temperature: 25° C.;
Integrating number: 10,000 times; and
Revolution: 4,000±500 rpm.

The electrophotographic photoreceptor of embodiments may be either a function-separation-type photoreceptor, in which a layer containing a charge generation substance (charge generation layer) and a layer containing a charge transfer substance (charge transfer layer) are separately provided, or a monolayer-type photoreceptor, in which both the charge generation layer and the charge transfer layer are contained in the same layer, as long as the electrophotographic photoreceptor of the particular embodiment has the photosensitive layer provided with the above-mentioned silicon compound-containing layer. The electrophotographic photoreceptor of the invention will be described in greater detail below, taking the function-separation-type photoreceptor as an example.

FIG. 1 is a cross-sectional view schematically showing an embodiment of the electrophotographic photoreceptor of the invention. The electrophotographic photoreceptor 1 shown in FIG. 1 is a function-separation-type photoreceptor in which a charge generation layer 13 and a charge transfer layer 14 are separately provided. That is, an underlayer 12, the charge generation layer 13, the charge transfer layer 14 and a protective layer 15 are laminated onto a conductive support 11 to form a photosensitive layer 16. The protective layer 15 contains a resin soluble in the liquid component contained in the coating solution used for formation of this layer and the silicon compound. Further, a peak area in the region of −40 to 0 ppm and a peak area in the region of −100 to −50 ppm in a $^{29}$Si—NMR spectrum of the photosensitive layer 16 satisfy equation (1).

The conductive support 11 may include, for example, a metal plate, a metal drum or a metal belt using a metal such as aluminum, copper, zinc, stainless steel, chromium, nickel, molybdenum, vanadium, indium, gold or a platinum, or an alloy thereof; and paper or a plastic film or belt coated, deposited or laminated with a conductive polymer, a conductive compound such as indium oxide, a metal such as aluminum, palladium or gold, or an alloy thereof. Further, surface treatment (such as anodic oxidation coating, hot water oxidation, chemical treatment, or coloring) or diffused reflection treatment (such as graining) can also be applied to a surface of the support 11.

Binding resins used in the underlayer 12 of embodiments may include but are not limited to, one or more polyamide resins, vinyl chloride resins, vinyl acetate resins, phenol resins, polyurethane resins, melamine resins, benzoguanamine resins, a polyimide resins, polyethylene resins, polypropylene resins, polycarbonate resins, acrylic resins, methacrylic resins, vinylidene chloride resins, polyvinyl acetal resins, vinyl chloride-vinyl acetate copolymers, polyvinyl alcohol resins, a water-soluble polyester resins, nitrocelluloses, caseins, gelatins, polyglutamic acids, starches, starch acetates, amino starches, polyacrylic acids, polyacrylamides, zirconium chelate compounds, titanyl chelate compounds, titanyl alkoxide compounds, organic titanyl compounds, silane coupling agents and mixtures thereof. Further, fine particles of titanium oxide, aluminum oxide, silicon oxide, zirconium oxide, barium titanate, a silicone resin or the like may be added to the above-mentioned binding resin in embodiments.

As a coating method in forming the underlayer of embodiments, an ordinary method such as blade coating, Mayer bar coating, spray coating, dip coating, bead coating, air knife coating or curtain coating may be employed. The thickness of the underlayer may be from about 0.01 to about 40 μm.

Non-limiting examples of charge generation substances that may be contained in the charge generation layer 13 of embodiments include, but are not limited to, various organic pigments and organic dyes; such as azo pigments, quinoline pigments, perylene pigments, indigo pigments, thioindigo pigments, bisbenzimidazole pigments, phthalocyanine pigments, quinacridone pigments, quinoline pigments, lake pigments, azo lake pigments, anthraquinone pigments, oxazine pigments, dioxazine pigments, triphenylmethane pigments, azulenium dyes, squalium dyes, pyrylium dyes, triallylmethane dyes, xanthene dyes, thiazine dyes and cyanine dyes; and inorganic materials such as amorphous silicon, amorphous selenium, tellurium, selenium-tellurium alloys, cadmium sulfide, antimony sulfide, zinc oxide and zinc sulfide. In embodiments, cyclocondensed aromatic pigments, perylene pigments and azo pigments may be used to impart sensitivity, electric stability and photochemical stability against irradiated light. These charge generation substances may be used either alone or as a combination of two or more.

In embodiments, the charge generation layer 13 may be formed by vacuum deposition of the charge generation substance or application of a coating solution in which the charge generation substance is dispersed in an organic solvent containing a binding resin. The binding resins used in the charge generation layer of embodiments include polyvinyl acetal resins such as polyvinyl butyral resins, polyvinyl formal resins or partially acetalized polyvinyl acetal resins in which butyral is partially modified with formal or acetoacetal, polyamide resins, polyester resins, modified ether type polyester resins, polycarbonate resins, acrylic resins, polyvinyl chloride resins, polyvinylidene chlorides, polystyrene resins, polyvinyl acetate resins, vinyl chloride-vinyl acetate copolymers, silicone resins, phenol resins, phenoxy resins, melamine resins, benzoguanamine resins, urea resins, polyurethane resins, poly-N-vinylcarbazole resins, polyvinylanthracene resins, polyvinylpyrene resins and mixtures thereof. In embodiments in which one or more of polyvinyl acetal resins, vinyl chloride-vinyl acetate copolymers, phenoxy resins or modified ether type polyester resins are used, the dispersibility of the charge generation substance may be improved to cause no occurrence of coagulation of the charge generation substance, and a coating solution that is stable for a long period of time may be obtained. The use of such a coating solution in embodiments makes it possible to form a uniform coating easily and surely. As a result, the electric characteristics may be improved, and image defects may be prevented. Further, the compounding ratio of the charge generation substance to the binding resin may be, in embodiments, within the range of from about 5:1 to about 1:2 by volume ratio.

Further, the solvents used in preparing the coating solution in embodiments may include organic solvents such as methanol, ethanol, n-propanol, n-butanol, benzyl alcohol, methyl cellosolve, ethyl cellosolve, acetone, methyl ethyl ketone, cyclohexanone, chlorobenzene, methyl acetate, n-butyl acetate, dioxane, tetrahydrofuran, methylene chloride, chloroform and mixtures thereof.

Methods for applying the coating solution in embodiments include the coating methods described above with reference to the underlayer. The thickness of the charge generation layer 13 thus formed may be from about 0.01 to about 5 μm, preferably from about 0.1 to about 2 μm. When the thickness of the charge generation layer 13 is less than 0.01 μm, it becomes difficult to uniformly form the charge generation layer. On the other hand, when the thickness exceeds 5 μm, the electrophotographic characteristics tend to significantly deteriorate.

Further, a stabilizer such as an antioxidant or an inactivating agent can also be added to the charge generation layer 13 in embodiments. Non-limiting examples of antioxidants that may be used include but are not limited to antioxidants such as phenolic, sulfur, phosphorus and amine compounds. Inactivating agents that may be used in embodiments may include bis(dithiobenzyl)nickel and nickel di-n-butylthiocarbamate.

In embodiments, the charge transfer layer 14 can be formed by applying a coating solution containing the charge transfer substance and a binding resin, and further fine particles, an additive, etc., as described above.

Low molecular weight charge transfer substances that may be used in embodiments may include, for example, pyrene, carbazole, hydrazone, oxazole, oxadiazole, pyrazoline, arylamine, arylmethane, benzidine, thiazole, stilbene and butadiene compounds. In embodiments, high molecular weight charge transfer substances may be used and include, for example, poly-N-vinylcarbazoles, poly-N-vinylcarbazole halides, polyvinyl pyrenes, polyvinylanthracenes, polyvinylacridines, pyrene-formaldehyde resins, ethylcarbazole-formaldehyde resins, triphenylmethane polymers and polysilanes. Triphenylamine compounds, triphenylmethane compounds and benzidine compounds may be used in embodiments to promote mobility, stability and transparency to light. Further, silicon compound represented by general formula (2) can also be used as charge transfer substances in particular embodiments.

As binding resins in embodiments, high molecular weight polymers that can form an electrical insulating film may be used. For example, when polyvinyl acetal resins, polyamide resins, cellulose resins, phenol resins, etc., which are soluble in alcoholic solvents, are used, binding resins used together with these resins include polycarbonates, polyesters, methacrylic resins, acrylic resins, polyvinyl chlorides, polyvinylidene chlorides, polystyrenes, polyvinyl acetates, styrene-butadiene copolymers, vinylidene chloride-acrylonitrile copolymers, vinyl chloride-vinyl acetate copolymers, vinyl chloride-vinyl acetate-maleic anhydride copolymers, silicone resins, silicone-alkyd resins, phenol-formaldehyde resins, styrene-alkyd resins, poly-N-vinylcarbazoles, polyvinyl butyrals, polyvinyl formals, polysulfones, casein, gelatin, polyvinyl alcohols, phenol resins, polyamides, carboxymethyl celluloses, vinylidene chloride-based polymer latexes and polyurethanes. Of the above-mentioned high molecular weight polymers, polycarbonates, polyesters, methacrylic resins and acrylic resins have excellent compatibility with the charge transfer substance, solubility and strength.

The charge transfer layer 14 of embodiments may further contain an additive such as a plasticizer, a surface modifier, an antioxidant or an agent for preventing deterioration by light.

The thickness of the charge transfer layer 14 may be, in embodiments, from about 5 to about 50 μm, preferably from about 10 to about 40 μm. When the thickness of the charge transfer layer is less than 5 μm, charging becomes difficult. However, thicknesses exceeding 50 μm result significant deterioration of the electrophotographic characteristics.

Protective layer 15 may contain, in embodiments, resins soluble in liquid components in coating solution used for formation of protective layers and silicon compounds as described above. Protective layer 15 may further contain a lubricant or fine particles of a silicone oil or a fluorine material, which can also improve lubricity and strength. Non-limiting examples of the lubricants include the above-mentioned fluorine-based silane coupling agents. Fine particles to be dispersed in the protective layer 15 of embodiments may include fine particles comprising resins obtained by copolymerizing fluororesins with hydroxyl group-containing monomers, as described in Proceedings of Lectures in the Eighth Polymer Material Forum, page 89, and semiconductive metal oxides, as well as the above-mentioned fine silicone particles and fine fluorine-based particles. The thickness of the protective layer may be, in embodiments, from about 0.1 to about 10 μm, preferably from about 0.5 to about 7 μm.

The electrophotographic photoreceptor of embodiments should not be construed as being limited to the abovementioned constitution. For example, the electrophotographic photoreceptor shown in FIG. 1 is provided with the protective layer 15. However, when the charge transfer layer 14 contains the resin soluble in the liquid component in the coating solution used for formation of this layer and the silicon compound, the charge transfer layer 14 may be used as a top surface layer (a layer on the side farthest apart from the support 11) without using the protective layer 15. In this case, the charge transfer substance contained in the charge transfer layer 14 is preferably soluble in the liquid component in the coating solution used for formation of the charge transfer layer 14. For example, when the coating solution used for formation of the charge transfer layer 14 contains the alcoholic solvent, the silicon compounds represented by the above-mentioned general formula (2) and compounds represented by the following formulas (VI-1) to (VI-16) are preferably used as the charge transfer substances.

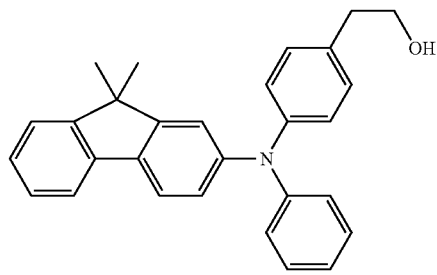
(VI-4)

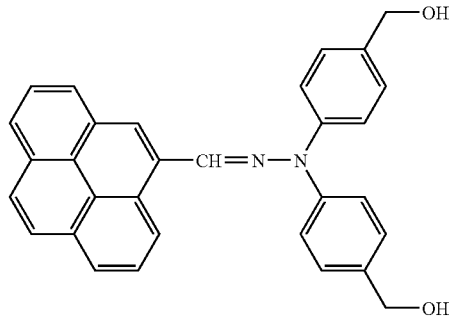
(VI-5)

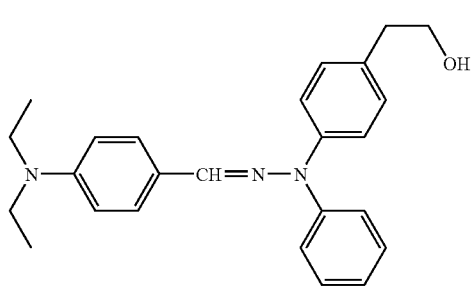
(VI-6)

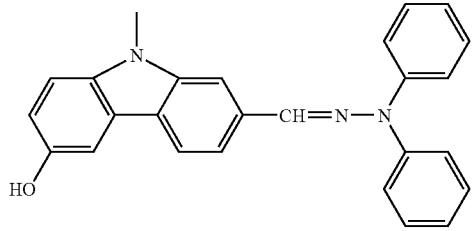
(VI-7)

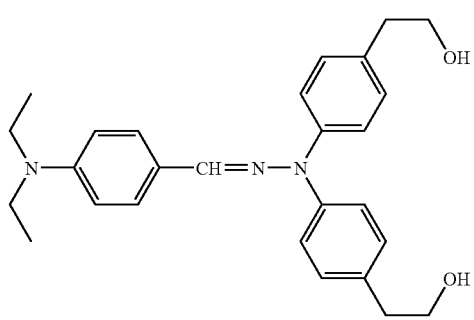
(VI-8)

(VI-1)

(VI-2)

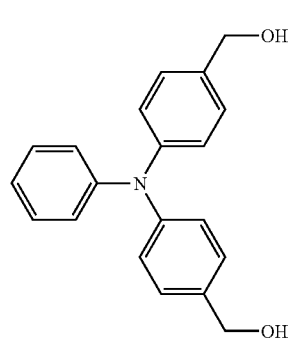

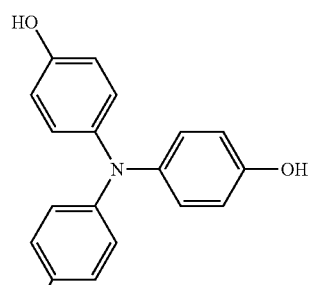

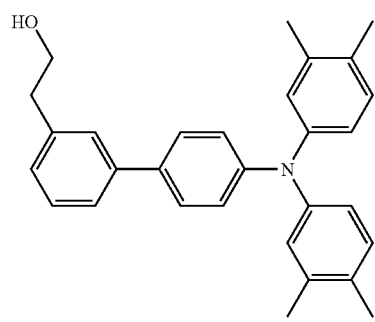
(VI-3)

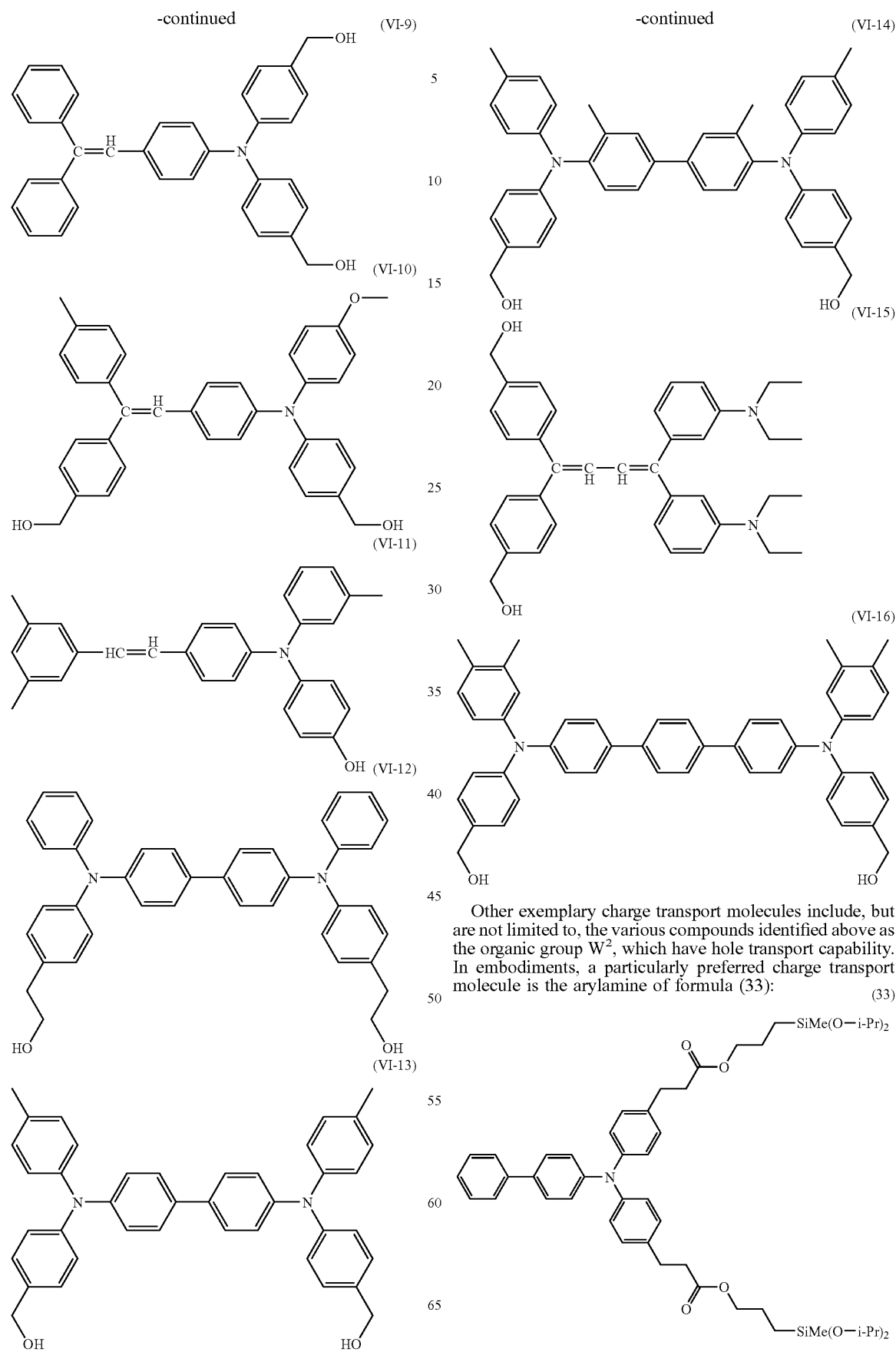
Other exemplary charge transport molecules include, but are not limited to, the various compounds identified above as the organic group $W^2$, which have hole transport capability. In embodiments, a particularly preferred charge transport molecule is the arylamine of formula (33):
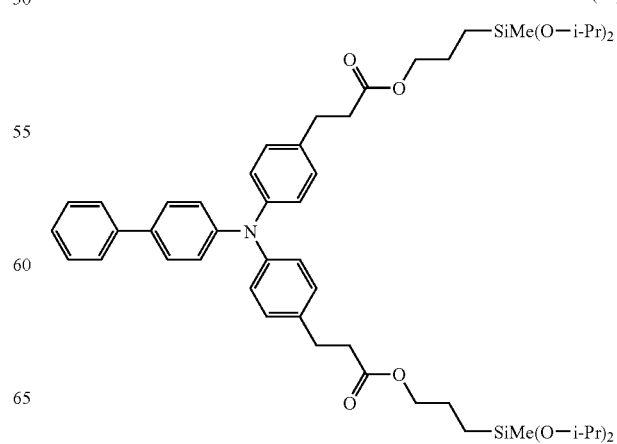

Production of such arylamine charge transport compounds, however, is generally a costly, time-consuming, multi-step process.

A process for producing this and other similar intermediate products is to utilize a direct hydrogenation reaction on an organic salt, in the process of converting a first disubstituted 4-aminobiphenyl compound into a second disubstituted 4-aminobiphenyl compound.

Figure 4:
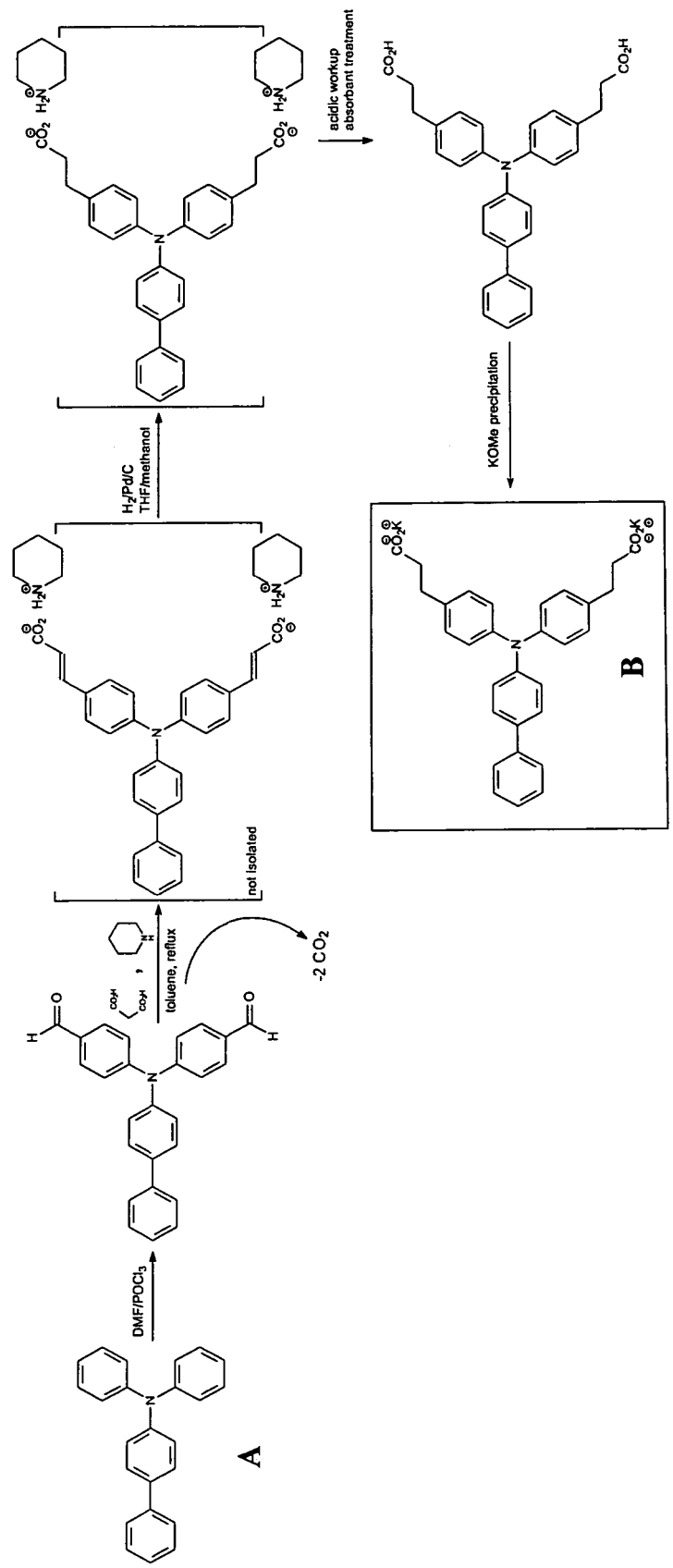
FIG. 4 sets forth a process for the production of an arylamine intermediate molecule, Compound B.
Figure 5:
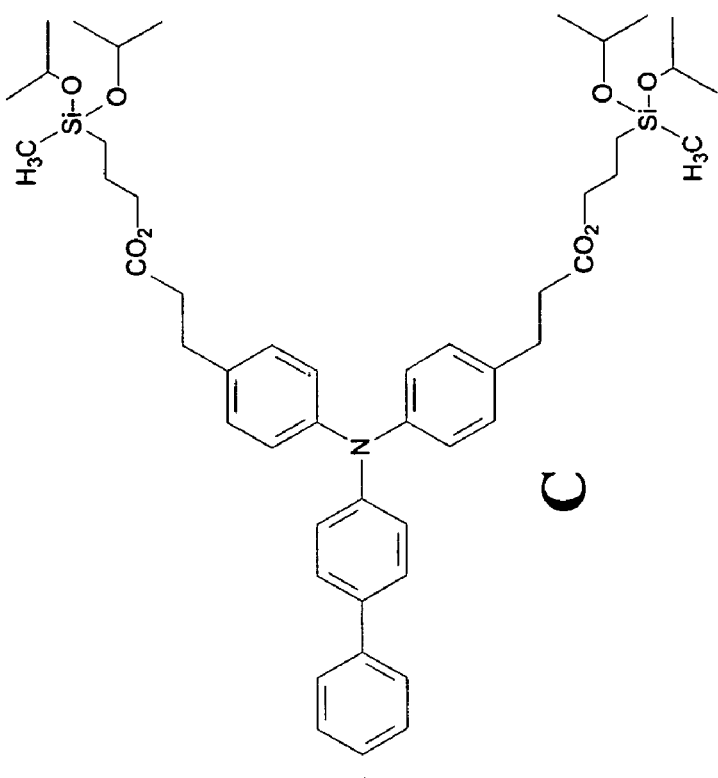
FIG. 5 sets forth a process for the production of an arylamine charge transporting molecule, Compound C.
Figure 5:
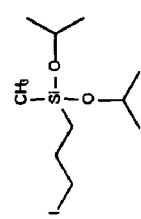
Figure 5:
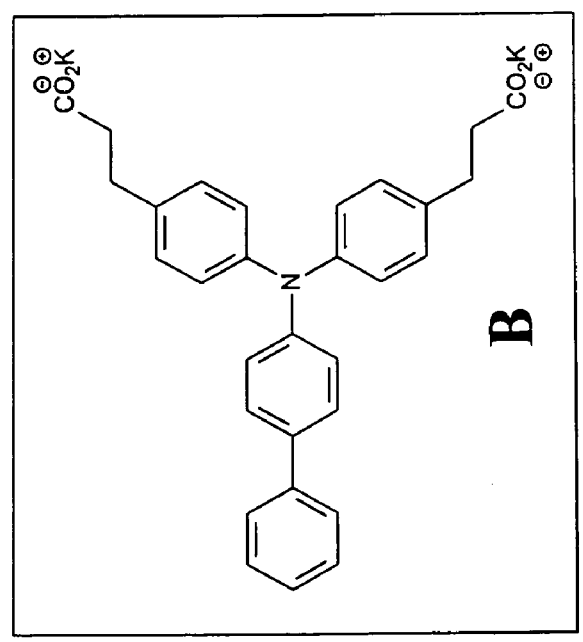

In a first step, a suitable first disubstituted 4-aminobiphenyl compound (shown as Compound A in FIG. 4) is formylated by means of a Vilsmeier (or Vilsmeier-Haack) reaction, to form a bisformyl substituted compound. Those skilled in the art will recognize there may be other ways and methods for the introduction of a formyl group into a compound of this type, for example by treatment of a halogenated derivative of the first disubstituted 4-aminobiphenyl compound (Compound A) with n-butyllithium followed by dimethylformamide (DMF) or treatment of such a compound with hexamethylene tetraamine in the presence of trifluoroacetic acid. One suitable method for forming bisformyl substituted compounds is disclosed in U.S. patent application Ser. No. 10/909,136 filed Jul. 30, 2004, the entire disclosure of which is incorporated herein by reference. Accordingly, neither the Vilsmeier (or Vilsmeier-Haack) reaction nor the n-butyllithium treatment nor the hexamethylene tetraamine treatment is meant to be an exhaustive list. Suitable examples of the first disubstituted 4-aminobiphenyl compound include, for example, compounds of the following general formula (34):

4-aminobiphenyl-$(R^1)(R^2)$       (34)

where $R^1$ and $R^2$, which can be the same or different, represent aromatic or heterocyclic groups. Suitable aromatic groups include, for example, substituted or unsubstituted phenyl groups; substituted or unsubstituted groups including two or more phenyl groups, such as biphenyl groups, triphenyl groups, and the like; substituted or unsubstituted fused polycyclic hydrocarbons, for example having from 2 to about 10 fused benzene rings, such as naphthyl groups, anthryl groups, phenanthryl groups, pyrenyl groups, and the like; and mixtures thereof. Suitable heterocyclic groups include, for example, substituted or unsubstituted 3- to 10-membered rings (preferably 5- or 6-membered rings) containing one or more heteroatoms, such as oxygen, sulfur, selenium, tellurium, nitrogen, phosphorus, arsenic, antimony, bismuth, silicon, germanium, tin, lead and mercury. Examples of such heterocyclic groups include, for example, substituted or unsubstituted groups selected from thiophene, pyridine, diazine, triazine, and the like. Substitution of these groups can be at one or more locations on the aromatic or heterocyclic ring(s), and can be by, for example, an alkyl groups of from 1 to about 15 carbon atoms, an alkenyl groups of from 1 to about 15 carbon atoms, alkynyl groups of from 1 to about 15 carbon atoms, halogen atoms, acid groups, ester groups, and the like. It will be appreciated by those skilled in the art that other compounds can also be used to provide a desired arylamine, and the invention is not limited to the above-listed compounds.

The first disubstituted 4-aminobiphenyl compound is subjected to a Vilsmeier reaction, to form a bisformyl substituted compound. Such formylation reactions are generally well known in the art, and thus are not described in detail herein. For example, N,N-diphenyl-4-aminobiphenyl can be formylated (bisformylated) by reacting the compound with dimethylformamide (DMF) and phosphorus oxychloride ($POCl_3$). The result is a compound of the following general formula (35):

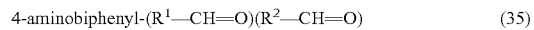
4-aminobiphenyl-$(R^1$—CH=O$)(R^2$—CH=O)       (35)

where $R^1$ and $R^2$ are as described above.

Of course, it will be recognized by those skilled in the art that the formylating reaction step can be omitted, where the first disubstituted 4-aminobiphenyl compound is already a bisformyl substituted compound. Thus, the formylating step is optional in those embodiments where the starting material is a formylated compound, but may be necessary where the starting material is not a formylated compound.

In a second step, the bisformylated compound of the first step is subjected to a condensation or modification reaction, preferably to convert the formyl end groups into acid groups. For example, the bisformylated compound of the first step can be subjected to a Knoevenagel condensation reaction, or specifically to a Doebner modification condensation reaction, to convert the —CH=O formyl end groups into —C=C—COOH carboxylic acid end groups. In embodiments, the Knoevenagel condensation reaction can be conducted by reaction of the bisformylated compound with an active methylene compound in the presence of an ammonia or an amine. Such Knoevenagel condensation reactions are also generally well known in the art, and thus are not described in detail herein.

A preferred active methylene compound is a malonic acid or ester, such as malonic acid. For toxicity reasons and ease of handling a preferred amine is piperidine, although ammonia, pyridine, and the like can also be used. The reaction can be conducted in a suitable solvent, such as toluene. Although the resultant acidified compound can be isolated from the reactants and solvent following completion of the reaction, such separation is not required. Thus, for example, in embodiments it is preferred that the reaction product mixture of the second step is used directly in the succeeding third step, described below, without purification or isolation.

In a third step, a hydrogenation reaction is used to directly and mildly hydrogenate unsaturated double bonds in the bisorganic salt compound, which in the preferred embodiments is a bispiperidine salt, produced in the second step. Such direct hydrogenation can be conducted in the presence of a suitable catalyst, such as a rhodium, palladium, platinum, raney nickel, or the like catalyst. The catalyst can be supported on a substrate, such as a carbon substrate, if desired. In embodiments, a 10% palladium on wet carbon catalyst is preferred.

For example, in one embodiment, the direct hydrogenation process can be performed under relatively low pressures of hydrogen gas, such as between 1 and 5 atmospheres, preferably between 1 and 2 atmospheres. After suitable reaction time, the absence of unsaturated double bonds can be confirmed, such as by using UV-Vis (ultraviolet visible) spectroscopy (where $A_{375\ nm}=0$) or by 1H NMR spectroscopy (CDCl3) indicating the absence of proton resonances for the protons on the unsaturated double bond (in the range of 6.0-6.8 ppm). The free saturated dicarboxylic acid can be freed from its piperidine salt by treatment of its solution with a suitable aqueous protic acid such as hydrochloric acid, nitric acid, sulfuric acid, or the like. For example, it has been found that the free dicarboxylic acid can discolor with time and exposure to air, so it is immediately converted to a salt of an alkali earth. Suitable alkali earths include, for example, lithium, sodium, potassium, rubidium, cesium, and francium, with potassium being preferred. In a preferred embodiment, the free dicarboxylic acid is treated with potassium methoxide or potassium isopropoxide in an alcoholic solution, the dicarboxylic acid is freely soluble in alcohols whereas the dipotassium salt is not.

The result of the process of the present invention is the formation of a desired arylamine compound, which can broadly be characterized as a derivative of 4-aminobiphenyl. Thus, for example, the arylamine compounds provided by the present invention can be represented by the following general formula (36):

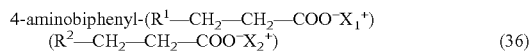
$$(R^2-CH_2-CH_2-COO^-X_2^+) \quad (36)$$

where $R^1$ and $R^2$, which can be the same or different, are as described above, and $X_1$ and $X_2$, which can be the same or different, are cationic groups, such as hydrogen ions ($H^+$), potassium ions ($K^+$), or the like.

After each step in the process, suitable separation, filtration, and purification processes can be conducted, as desired. For example, after the third step, the final product can be isolated, for example, by a suitable recrystallization procedure. All of these procedures are conventional and will be apparent to those skilled in the art. However, a benefit of the invention, as described above, is that the reaction product mixture from the second step can be directly used in the third step without isolation or purification.

Image Forming Apparatus and Process Cartridge

Figure 2:
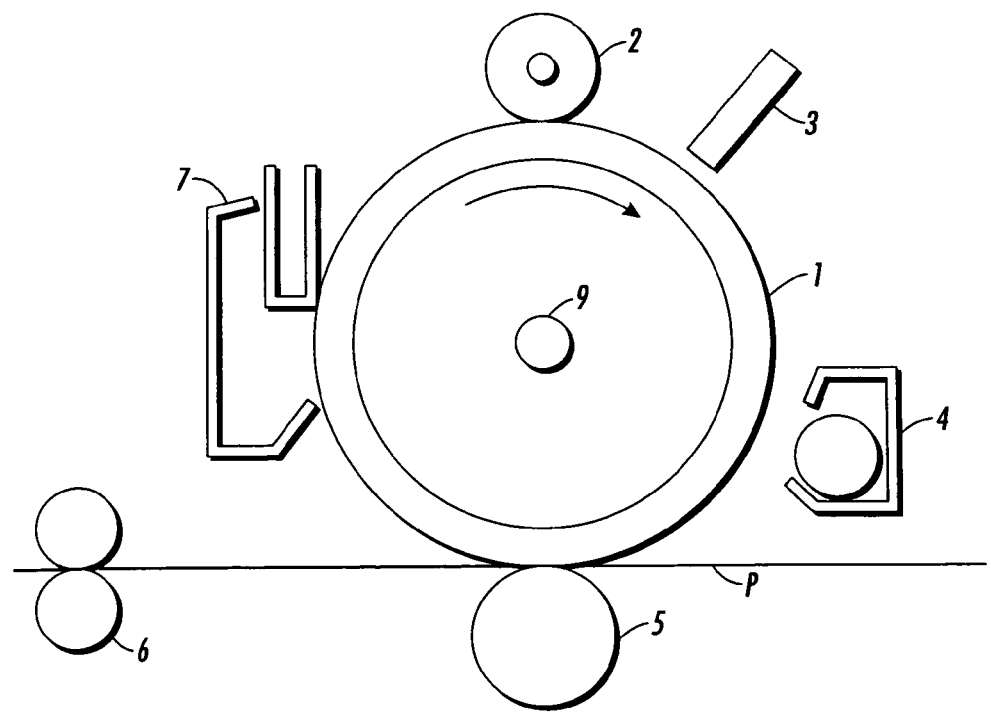
FIG. 2 is a schematic view showing a preferred embodiment of an image forming apparatus of the invention.

FIG. 2 is a schematic view showing an embodiment of an image forming apparatus. In the apparatus shown in FIG. 2, the electrophotographic photoreceptor 1 constituted as shown in FIG. 1 is supported by a support 9, and rotatable at a specified rotational speed in the direction indicated by the arrow, centered on the support 9. A contact charging device 2, an exposure device 3, a developing device 4, a transfer device 5 and a cleaning unit 7 are arranged in this order along the rotational direction of the electrophotographic photoreceptor 1. Further, this exemplary apparatus is equipped with an image fixing device 6, and a medium P to which a toner image is to be transferred is conveyed to the image fixing device 6 through the transfer device 5.

The contact charging device 2 has a roller-shaped contact charging member. The contact charging member is arranged so that it comes into contact with a surface of the photoreceptor 1, and a voltage is applied, thereby being able to give a specified potential to the surface of the photoreceptor 1. In embodiments, a contact charging member may be formed from a metal such as aluminum, iron or copper, a conductive polymer material such as a polyacetylene, a polypyrrole or a polythiophene, or a dispersion of fine particles of carbon black, copper iodide, silver iodide, zinc sulfide, silicon carbide, a metal oxide or the like in an elastomer material such as polyurethane rubber, silicon rubber, epichlorohydrin rubber, ethylene-propylene rubber, acrylic rubber, fluororubber, styrene-butadiene rubber or butadiene rubber. Non-limiting examples of metal oxides that may be used in embodiments include $ZnO$, $SnO_2$, $TiO_2$, $In_2O_3$, $MoO_3$ and complex oxides thereof. Further, a perchlorate may be added to the elastomer material to impart conductivity.

Further, a covering layer can also be provided on a surface of the contact charging member of embodiments. Non-limiting examples of materials that may be used in embodiments for forming a covering layer include N-alkoxy-methylated nylon, cellulose resins vinylpyridine resins, phenol resins, polyurethanes, polyvinyl butyrals, melamines and mixtures thereof. Furthermore, emulsion resin materials such as acrylic resin emulsions, polyester resin emulsions or polyurethanes, may be used. In order to further adjust resistivity, conductive agent particles may be dispersed in these resins, and in order to prevent deterioration, an antioxidant can also be added thereto. Further, in order to improve film forming properties in forming the covering layer, a leveling agent or a surfactant may be added to the emulsion resin in embodiments of the invention.

The resistance of the contact charging member of embodiments may be from $10^0$ to $10^{14}$ $\Omega$cm, and from $10^2$ to $10^{12}$ $\Omega$cm. When a voltage is applied to this contact charging member, either a DC voltage or an AC voltage can be used as the applied voltage. Further, a superimposed voltage of a DC voltage and an AC voltage can also be used.

In the exemplary apparatus shown in FIG. 2, the contact charging member of the contact charging device 2 is in the shape of a roller. However, such a contact charging member may be in the shape of a blade, a belt, a brush or the like.

Further, in embodiments an optical device that can perform desired imagewise exposure to a surface of the electrophotographic photoreceptor 1 with a light source such as a semiconductor laser, an LED (light emitting diode) or a liquid crystal shutter, may used as the exposure device 3.

Furthermore, a known developing device using a normal or reversal developing agent of a one-component system, a two-component system or the like may be used in embodiments as the developing device 4. There is no particular limitation on toners that may be used in embodiments of the invention.

Contact type transfer charging devices using a belt, a roller, a film, a rubber blade or the like, or a scorotron transfer charger or a corotron transfer charger utilizing corona discharge may be employed as the transfer device 5, in various embodiments.

Further, in embodiments, the cleaning device 7 may be a device for removing a remaining toner adhered to the surface of the electrophotographic photoreceptor 1 after a transfer step, and the electrophotographic photoreceptor 1 repeatedly subjected to the above-mentioned image formation process may be cleaned thereby. In embodiments, the cleaning device 7 may be a cleaning blade, a cleaning brush, a cleaning roll or the like. Materials for the cleaning blade include urethane rubber, neoprene rubber and silicone rubber.

In the exemplary image forming device shown in FIG. 2, the respective steps of charging, exposure, development, transfer and cleaning are conducted in turn in the rotation step of the electrophotographic photoreceptor 1, thereby repeatedly performing image formation. The electrophotographic photoreceptor 1 may be provided with specified silicon compound-containing layers and photosensitive layers that satisfy equation (1), as described above, and thus photoreceptors having excellent discharge gas resistance, mechanical strength, scratch resistance, particle dispersibility, etc., may be provided. Accordingly, even in embodiments in which the photoreceptor is used together with the contact charging device or the cleaning blade, or further with spherical toner obtained by chemical polymerization, good image quality can be obtained without the occurrence of image defects such as fogging. That is, embodiments of the invention provide image forming apparatuses that can stably provide good image quality for a long period of time is realized.

Figure 3:
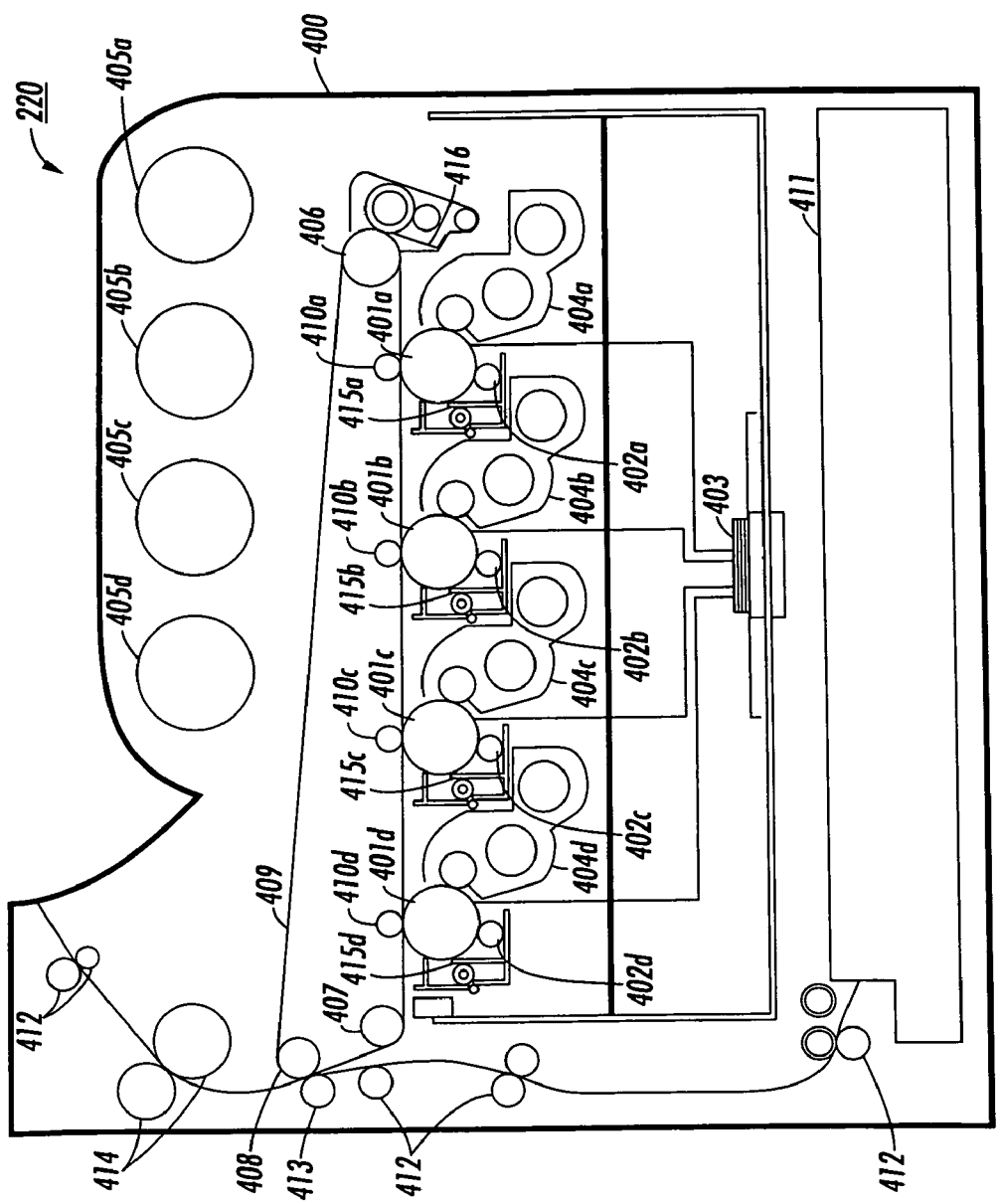
FIG. 3 is a schematic view showing another preferred embodiment of an image forming apparatus of the invention.

FIG. 3 is a cross sectional view showing another exemplary embodiment of an image forming apparatus. The image forming apparatus 220 shown in FIG. 3 is an image forming apparatus of an intermediate transfer system, and four electrophotographic photoreceptors 401a to 401d are arranged in parallel with each other along an intermediate transfer belt 409 in a housing 400.

Here, the electrophotographic photoreceptors 401a to 401d carried by the image forming apparatus 220 are each the electrophotographic photoreceptor of the invention. Each of the electrophotographic photoreceptors 401a to 401d may rotate in a predetermined direction (counterclockwise on the sheet of FIG. 3), and charging rolls 402a to 402d, developing device 404a to 404d, primary transfer rolls 410a to 410d and cleaning blades 415a to 415d are each arranged along the rotational direction thereof. In each of the developing device 404a to 404d, four-color toners of yellow (Y), magenta (M), cyan (C) and black (B) contained in toner cartridges 405a to 405d can be supplied, and the primary transfer rolls 410a to 410d are each brought into abutting contact with the electrophotographic photoreceptors 401a to 401d through an intermediate transfer belt 409.

Further, a laser light source (exposure unit) 403 is arranged at a specified position in the housing 400, and it is possible to irradiate surfaces of the electrophotographic photoreceptors 401a to 401d after charging with laser light emitted from the laser light source 403. This performs the respective steps of charging, exposure, development, primary transfer and cleaning in turn in the rotation step of the electrophotographic photoreceptors 401a to 401d, and toner images of the respective colors are transferred onto the intermediate transfer belt 409, one over the other.

The intermediate transfer belt 409 is supported with a driving roll 406, a backup roll 408 and a tension roll 407 at a specified tension, and rotatable by the rotation of these rolls without the occurrence of deflection. Further, a secondary transfer roll 413 is arranged so that it is brought into abutting contact with the backup roll 408 through the intermediate transfer belt 409. The intermediate transfer belt 409 which has passed between the backup roll 408 and the secondary transfer roll 413 is cleaned up by a cleaning blade 416, and then repeatedly subjected to the subsequent image formation process.

Further, a tray (tray for a medium to which a toner image is to be transferred) 411 is provided at a specified position in the housing 400. The medium to which the toner image is to be transferred (such as paper) in the tray 411 is conveyed in turn between the intermediate transfer belt 409 and the secondary transfer roll 413, and further between two fixing rolls 414 brought into abutting contact with each other, with a conveying roll 412, and then delivered out of the housing 400.

According to the exemplary image forming apparatus 220 shown in FIG. 3, the use of electrophotographic photoreceptors of embodiments of the invention as electrophotographic photoreceptors 401a to 401d may achieve discharge gas resistance, mechanical strength, scratch resistance, etc. on a sufficiently high level in the image formation process of each of the electrophotographic photoreceptors 401a to 401d. Accordingly, even when the photoreceptors are used together with the contact charging devices or the cleaning blades, or further with the spherical toner obtained by chemical polymerization, good image quality can be obtained without the occurrence of image defects such as fogging. Therefore, also according to the image forming apparatus for color image formation using the intermediate transfer body, such as this embodiment, the image forming apparatus which can stably provide good image quality for a long period of time is realized.

The invention should not be construed as being limited to the above-mentioned embodiments. For example, each apparatus shown in FIG. 2 or 3 may be equipped with a process cartridge comprising the electrophotographic photoreceptor 1 (or the electrophotographic photoreceptors 401a to 401d) and charging device 2 (or the charging devices 402a to 402d). The use of such a process cartridge allows maintenance to be performed more simply and easily.

Further, in embodiments, when a charging device of the non-contact charging system such as a corotron charger is used in place of the contact charging device 2 (or the contact charging devices 402a to 402d), sufficiently good image quality can be obtained.

Furthermore, in the embodiment of an apparatus that is shown in FIG. 2, a toner image formed on the surface of the electrophotographic photoreceptor 1 is directly transferred to the medium P to which the toner image is to be transferred. However, the image forming apparatus of the invention may be further provided with an intermediate transfer body. This makes it possible to transfer the toner image from the intermediate transfer body to the medium P to which the toner image is to be transferred, after the toner image on the surface of the electrophotographic photoreceptor 1 has been transferred to the intermediate transfer body. As such an intermediate transfer body, there can be used one having a structure in which an elastic layer containing a rubber, an elastomer, a resin or the like and at least one covering layer are laminated on a conductive support.

In addition, the image forming apparatus of embodiments may be further equipped with a static eliminator such as an erase light irradiation device. This may prevent incorporation of residual potential into subsequent cycles when the electrophotographic photoreceptor is used repeatedly. Accordingly, image quality can be more improved.

EXAMPLES

The invention will be illustrated in greater detail with reference to the following Examples and Comparative Examples, but the invention should not be construed as being limited thereto. In the following examples and comparative examples, all the "parts" are given by weight unless otherwise indicated.

Example 1

Preparation of Arylamine Intermediate

To a 2-liter 3-necked flask is fitted an argon inlet, mechanical stirrer, and Dean-Stark trap. The flask is charged with 103.5 g bisformyl-N,N-diphenyl-4-aminobiphenyl dissolved in 400 mL toluene. To this, 114.4 g malonic acid and 93.6 g piperidine are added. After an initial exotherm, has subsided, the reaction vessel is heated at reflux overnight. 200 mL toluene is distilled off, and then the reaction is diluted with 250 mL THF (tetrahydrofuran), which is initiator free, and 250 mL methanol. 3 g of palladium on charcoal (10%, wet) is added and the reaction vessel is placed under an atmosphere of hydrogen (1-2 atm.). The reaction is stirred at room temperature overnight, and then diluted with 1 L ethylacetate and washed successively with 10 wt % sulfuric acid (3 times with 500 mL each time), 10 wt % Rochelle salt (1 time at 500 mL), and saturated sodium chloride (I time at 500 mL). The ethylacetate is dried and removed. The residue is dissolved in methanol (200 mL), and 38.2 g potassium methoxide is added. The homogeneous solution is stirred for 1 hour at room temperature. Next, 800 mL isopropanol is added and the mixture is distilled to remove 500 mL without recirculation. The mixture is cooled, and 500 mL heptane is added to complete the precipitation. The solid is filtered and washed with 500 mL heptane and dried under vacuum at 50° C. overnight. The yield is 87.9 g N,N-[3-carboxypropyl phenyl]-4-aminobiphenyl dipotassium salt at an overall 60% yield.

Example 2

Preparation of Arylamine Intermediate

To a 2-liter 3-necked flask is fitted an argon inlet, mechanical stirrer, and Dean-Stark trap. The flask is charged with 37 g bisformyl-N,N-diphenyl-4-aminobiphenyl dissolved in 165 mL toluene. To this, 40.9 g malonic acid and 33.5 g piperidine are added. After an initial exotherm, has subsided, the reaction vessel is heated at reflux overnight. 90 mL toluene is distilled off, and then the reaction is diluted with 90 mL THF (tetrahydrofuran), which is initiator free, and 90 mL methanol. 1.1 g of palladium on charcoal (10%, wet) is added and the reaction vessel is placed under an atmosphere of hydrogen (1-2 atm.). The reaction is stirred at room temperature overnight, and then diluted with 360 mL ethylacetate and washed successively with 10 wt % sulfuric acid (3 times with 165 mL each time), 10 wt % Rochelle salt (1 time at 165 mL), and saturated sodium chloride (1 time at 165 mL). The ethylacetate is collected and 11.5 g clay is added and the mixture heated to a boil and then filtered while hot. The filtrate is collected, dried, and removed. The residue is dissolved in methanol (70 mL), and 13.6 g potassium methoxide is added. The homogeneous solution is stirred for 1 hour at room temperature. Next, 290 mL isopropanol is added. The flask is fitted with a fractionating column and the mixture is distilled to remove 100 mL without recirculation at a boiling point between 72 and 75° C. An additional 100 mL isopropanol is added, and 100 mL is removed without recirculation until a boiling point of 82° C. is achieved. The mixture is cooled, and 180 mL heptane is added to complete the precipitation. The solid is filtered and washed with 180 mL heptane. The solid is dissolved in 70 ml methanol and 0.270 g (2 mol %) potassium methoxide is added. The homogeneous solution is stirred for 1 hour at room temperature. Next, 290 mL isopropanol is added. The flask is fitted with a fractionating column and the mixture is distilled to remove 100 mL without recirculation at a boiling point between 72 and 75° C. An additional 100 mL isopropanol is added, and 100 mL is removed without recirculation until a boiling point of 82° C. is achieved. The mixture is cooled, and 180 mL heptane is added to complete the precipitation. The solid is filtered and washed with 180 mL heptane and dried under vacuum at 50° C. overnight. The yield is 35.2 g N,N-[3-carboxypropyl phenyl]-4-aminobiphenyl dipotassium salt at an overall 66% yield.

Example 3

Preparation of Arylamine Charge Transport Molecule

In a suitable reaction apparatus, the material from Example 1 (116 g) is dissolved in a mixture of DMF (200 mL), isopropyl alcohol (IPA, 100 mL) and 3-iodopropylmethyldiisopropoxysilane (111 g) is added and the mixture heated at 90° C. under an atmosphere of nitrogen for 5 hours after which the mixture is cooled to room temperature. Toluene (500 mL) is added and the solution is washed with water and saturated sodium chloride solution. On removal of the volatile organic solvents and chromatographing on silica gel, the compound (33) can be obtained in suitable purity for application in the preparation of siloxane containing charge transporting layers for electrophotographic application.

Example 4

Preparation of Photoreceptor Layer 11 parts of compound (33), 5.8 parts of compound III-3, 0.2 parts of 1-(dimethoxymethylsilyl)-1H,2H,2H-perfluorononane, 1 part of hexamethylcyclotrisilane and 11 parts of methanol were mixed, and 2 parts of an ion exchange resin (AMBERLIST H15) was added thereto, followed by stirring for 2 hours. Furthermore, 32 parts of butanol and 4.92 parts of distilled water were added to this mixture, followed by stirring at room temperature for 30 minutes. Then, the resulting mixture was filtered to remove the ion exchange resin, and 0.180 parts of aluminum trisacetylacetonate (Al (AcAc)$_3$), 0.180 parts of acetylacetone (AcAc), 2 parts of a polyvinyl butyral resin (trade name: S-LEC KW-1, manufactured by Sekisui Chemical Co., Ltd.), 0.0180 parts of butylated-hydroxytoluene (BHT) and 0.261 parts of a hindered phenol antioxidant (IRGANOX 1010) were added to a filtrate obtained, and thoroughly dissolved therein for 2 hours to obtain a coating solution for a protective layer. This coating solution was applied onto the above-mentioned charge transfer layer by dip coating (coating speed: about 170 mm/min), and dried by heating at 130° C. for one hour to form the protective layer having a film thickness of 3 µm, thereby obtaining a desired electrophotographic photoreceptor.

While the invention has been described in detail and with reference to specific embodiments thereof, it will be apparent to one skilled in the art that various changes and modifications can be made therein without departing from the spirit and scope thereof.

What is claimed is:

1. A process for forming a 4-aminobiphenyl derivative arylamine compound, comprising:
   (i) providing a first disubstituted 4-aminobiphenyl compound;
   (ii) optionally formylating said first disubstituted 4-aminobiphenyl compound to form a bisformyl substituted compound, where said first disubstituted 4-aminobiphenyl compound is not a bisformyl substituted compound;
   (iii) acidifying said bisformyl substituted compound to convert formyl functional groups into acid functional groups to form an acidified compound; and
   (iv) hydrogenating said acidified compound to saturate at least one unsaturated double bonds in the acidified compound,
   wherein there is provided a second disubstituted 4-aminobiphenyl compound.

2. The process according to claim 1, wherein said first disubstituted 4-aminobiphenyl compound is represented by the following general formula:

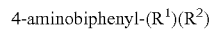
4-aminobiphenyl-(R$^1$)(R$^2$)

where R$^1$ and R$^2$, which can be the same or different, represent aromatic or heterocyclic groups.

3. The process according to claim 2, wherein R$^1$ and R$^2$ are the same.

4. The process according to claim 2, wherein R$^1$ and R$^2$ are different.

5. The process according to claim 2, wherein R$^1$ and R$^2$ are aromatic groups selected from the group consisting of substituted or unsubstituted phenyl groups, substituted or unsubstituted groups including two or more phenyl groups, substituted or unsubstituted fused polycyclic hydrocarbons, and mixtures thereof.

6. The process according to claim 2, wherein $R^1$ and $R^2$ are heterocyclic groups selected from the group consisting of substituted or unsubstituted 3- to 10-membered rings containing one or more heteroatoms.

7. The process according to claim 1, wherein said formylating is conducted by way of a Vilsmeier reaction.

8. The process according to claim 1, wherein said formylating is conducted by treating a halogenated derivative of the first disubstituted 4-aminobiphenyl compound with n-butyllithium followed by dimethytlformamide.

9. The process according to claim 1, wherein said formylating is conducted by treating a halogenated derivative of the first disubstituted 4-aminobiphenyl compound with hexamethylene tetraamine in the presence of trifluoroacetic acid.

10. The process according to claim 1, wherein said first disubstituted 4-aminobiphenyl compound is a bisformyl substituted compound represented by the following general formula:

4-aminobiphenyl-$(R^1)(R^2)$ where $R^1$ and $R^2$, which can be the same or different, represent aromatic or heterocyclic groups.

11. The process according to claim 2, wherein said bisformyl substituted compound is represented by the following general formula:

4-aminobiphenyl-$(R^1$—CH=O$)(R^2$—CH=O$)$.

12. The process according to claim 1, wherein said acidifying comprises a condensation reaction.

13. The process according to claim 1, wherein said acidifying is conducted by way of a Knoevenagel condensation reaction.

14. The process according to claim 1, wherein said acidifying is conducted by way of a Doebner modification condensation reaction.

15. The process according to claim 1, wherein said acidifying converts —CH=O formyl functional end groups into —C=C—COOH carboxylic acid functional end groups.

16. The process according to claim 2, wherein said acidified compound is represented by the following general formula:

4-aminobiphenyl-$(R^1$—C=C—COOH$)(R^2$—C=C—COOH$)$.

17. The process according to claim 1, wherein said acidified compound is used directly in the step (iii) without purification or isolation.

18. The process according to claim 1, wherein said hydrogenating is conducted in the presence of a catalyst.

19. The process according to claim 8, wherein said catalyst is supported on a carbon substrate.

20. The process according to claim 1, wherein said second disubstituted 4-aminobiphenyl compounds is a carboxylic acid compound.

21. The process according to claim 1, further comprising forming an alkali metal salt of the second disubstituted 4-aminobiphenyl compound.

22. The process according to claim 2, wherein said second disubstituted 4-aminobiphenyl compound is represented by the following general formula:

4-aminobiphenyl-$(R^1$—CH$_2$—CH$_2$—COO$^-$X$_1^+)$
$(R^2$—CH$_2$—CH$_2$—COO$^-$X$_2^+)$ wherein $X_1$ and $X_2$, which can be the same or different, are cationic groups.

23. The process according to claim 22, wherein said cationic groups are alkali metals.

* * * * *